(12) United States Patent
Bourne et al.

(10) Patent No.: US 9,895,523 B2
(45) Date of Patent: *Feb. 20, 2018

(54) IMPLANTABLE MEDICAL DEVICE FOR IMPROVED PLACEMENT AND ADHERENCE IN THE BODY

(71) Applicant: Navilyst Medical Inc., Marlborough, MA (US)

(72) Inventors: George Bourne, Boston, MA (US); James Culhane, Westborough, MA (US)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/856,680

(22) Filed: Sep. 17, 2015

(65) Prior Publication Data

US 2016/0001055 A1 Jan. 7, 2016

Related U.S. Application Data

(63) Continuation of application No. 14/070,134, filed on Nov. 1, 2013, now Pat. No. 9,168,365, which is a
(Continued)

(51) Int. Cl.
*A61M 39/02* (2006.01)
*A61M 39/04* (2006.01)
*A61M 5/14* (2006.01)

(52) U.S. Cl.
CPC ........ *A61M 39/0208* (2013.01); *A61M 39/04* (2013.01); *A61M 5/1415* (2013.01);
(Continued)

(58) Field of Classification Search
CPC .......... A61M 39/0208; A61M 39/0247; A61M 39/04; A61M 2039/0211;
(Continued)

(56) References Cited

U.S. PATENT DOCUMENTS 3,094,124 A 6/1963 Birtwell
3,438,375 A 4/1969 Ericson
(Continued)

FOREIGN PATENT DOCUMENTS

WO WO9818506 5/1998

OTHER PUBLICATIONS

McCarthy, et al, The Use of a Flow Rate Injctor for Contrast-Enhanced CT, Radiology, 1984, 151:800.
(Continued)

*Primary Examiner* — Theodore Stigell
(74) *Attorney, Agent, or Firm* — Zachary F. Madonna

(57) ABSTRACT

A medical device comprises a flexible member that can be adhesively attached to a housing of the medical device, allowing implantation of the medical device into a body through an incision of reduced size. The flexible member can be attached to the housing either before or after implantation into the body. The flexible member comprises suture locations, including a permeable membrane or a suture hole, for suturing the medical device to tissue of the body. The suture holes can be filled with a substance penetrable by a suture needle, to minimize tissue ingrowth before or after suturing.

15 Claims, 13 Drawing Sheets

Related U.S. Application Data continuation of application No. 10/277,215, filed on Oct. 21, 2002, now Pat. No. 8,574,204.

(52) U.S. Cl.
CPC .............. *A61M 2039/0211* (2013.01); *A61M 2039/0223* (2013.01); *A61M 2039/0232* (2013.01)

(58) Field of Classification Search
CPC .. A61M 2039/0223; A61M 2039/0229; A61M 2039/0232
See application file for complete search history.

(56) References Cited

U.S. PATENT DOCUMENTS

| | | |
|---|---|---|
| 3,971,376 A | 7/1976 | Wichterle |
| 3,978,157 A | 8/1976 | Bottenbruch et al. |
| 4,054,139 A | 10/1977 | Crossley |
| 4,142,525 A | 3/1979 | Binard et al. |
| 4,245,635 A | 1/1981 | Kontos |
| 4,248,224 A | 2/1981 | Jones |
| 4,309,994 A | 1/1982 | Grunwald |
| 4,403,983 A | 9/1983 | Edelman et al. |
| 4,405,305 A | 9/1983 | Stephen et al. |
| 4,423,740 A | 1/1984 | Castle et al. |
| 4,425,119 A | 1/1984 | Berglund |
| 4,468,224 A | 8/1984 | Enzmann et al. |
| 4,469,483 A | 9/1984 | Becker et al. |
| 4,483,688 A | 11/1984 | Akiyama |
| 4,543,088 A | 9/1985 | Bootman et al. |
| 4,563,180 A | 1/1986 | Jervis et al. |
| 4,569,673 A | 2/1986 | Tesi |
| 4,571,749 A | 2/1986 | Fischell |
| 4,587,954 A | 5/1986 | Haber |
| 4,592,920 A | 6/1986 | Murtfeldt |
| 4,603,152 A | 7/1986 | Laurin et al. |
| 4,623,327 A | 11/1986 | Mahurkar |
| 4,645,495 A | 2/1987 | Vaillancourt |
| 4,673,394 A | 6/1987 | Fenton, Jr. et al. |
| 4,692,146 A | 9/1987 | Hilger |
| 4,710,174 A | 12/1987 | Moden et al. |
| 4,767,410 A | 8/1988 | Moden et al. |
| 4,769,005 A | 9/1988 | Ginsburg et al. |
| 4,778,452 A | 10/1988 | Moden et al. |
| 4,781,680 A | 11/1988 | Redmond et al. |
| 4,781,695 A | 11/1988 | Dalton |
| 4,804,359 A | 2/1989 | Grunwald et al. |
| 4,808,156 A | 2/1989 | Dean |
| 4,822,341 A | 4/1989 | Colone |
| 4,838,873 A | 6/1989 | Landskron et al. |
| 4,857,053 A | 8/1989 | Dalton |
| 4,886,501 A | 12/1989 | Johnston et al. |
| 4,886,502 A | 12/1989 | Poirier et al. |
| 4,892,518 A | 1/1990 | Cupp et al. |
| 4,897,081 A | 1/1990 | Poirier et al. |
| 4,902,503 A | 2/1990 | Umemura et al. |
| 4,929,236 A | 5/1990 | Sampson |
| 4,944,726 A | 7/1990 | Hilal et al. |
| 4,954,130 A | 9/1990 | Edwards |
| 4,955,861 A | 9/1990 | Enegren et al. |
| 4,966,586 A | 10/1990 | Vaillancourt |
| 4,983,162 A | 1/1991 | Metais et al. |
| 5,013,304 A | 5/1991 | Russell et al. |
| 5,019,096 A | 5/1991 | Fox, Jr. et al. |
| 5,041,098 A | 8/1991 | Loiterman et al. |
| 5,053,013 A | 10/1991 | Ensminger et al. |
| 5,059,170 A | 10/1991 | Cameron |
| 5,069,206 A | 12/1991 | Crosbie |
| 5,084,015 A | 1/1992 | Moriuchi |
| 5,092,849 A | 3/1992 | Sampson |
| 5,125,893 A | 6/1992 | Dryden |
| 5,129,891 A | 7/1992 | Young |
| 5,133,742 A | 7/1992 | Pinchuk |
| 5,137,529 A * | 8/1992 | Watson ............ A61M 39/0208 128/DIG. 12 |
| 5,151,231 A | 9/1992 | Lambert et al. |
| 5,167,638 A | 12/1992 | Felix et al. |
| 5,171,305 A | 12/1992 | Schickling et al. |
| 5,178,612 A | 1/1993 | Fenton, Jr. |
| 5,180,365 A | 1/1993 | Ensminger et al. |
| 5,203,771 A | 4/1993 | Melker et al. |
| 5,205,834 A | 4/1993 | Moorehead et al. |
| 5,213,574 A | 5/1993 | Tucker |
| D337,637 S | 7/1993 | Tucker |
| 5,229,431 A | 7/1993 | Pinchuk |
| 5,236,417 A | 8/1993 | Wallis |
| 5,242,415 A | 9/1993 | Kantrowitz et al. |
| 5,249,598 A | 10/1993 | Schmidt |
| 5,250,038 A | 10/1993 | Melker et al. |
| 5,263,930 A | 11/1993 | Ensminger |
| 5,281,199 A | 1/1994 | Ensminger et al. |
| 5,281,205 A | 1/1994 | McPherson |
| 5,300,048 A | 4/1994 | Drewes, Jr. et al. |
| 5,312,337 A | 5/1994 | Flaherty et al. |
| 5,318,545 A | 6/1994 | Tucker |
| 5,330,449 A | 7/1994 | Prichard et al. |
| 5,350,360 A | 9/1994 | Ensminger et al. |
| 5,352,204 A | 10/1994 | Ensminger |
| 5,356,381 A | 10/1994 | Ensminger et al. |
| 5,370,624 A | 12/1994 | Edwards et al. |
| 5,372,582 A | 12/1994 | Skrabal et al. |
| 5,373,855 A | 12/1994 | Skrabal et al. |
| 5,387,192 A | 2/1995 | Glantz et al. |
| 5,399,168 A | 3/1995 | Wadsworth, Jr. et al. |
| 5,403,291 A | 4/1995 | Abrahamson |
| 5,405,340 A | 4/1995 | Fageol et al. |
| 5,417,656 A | 5/1995 | Ensminger et al. |
| 5,421,814 A | 6/1995 | Geary |
| 5,423,334 A | 6/1995 | Jordan |
| 5,458,582 A | 10/1995 | Nakao |
| 5,476,451 A | 12/1995 | Ensminger et al. |
| 5,509,897 A | 4/1996 | Twardowski et al. |
| 5,520,632 A | 5/1996 | Leveen et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,527,307 A | 6/1996 | Srisathapat et al. |
| 5,531,684 A | 7/1996 | Ensminger et al. |
| 5,542,923 A | 8/1996 | Ensminger et al. |
| 5,542,937 A | 8/1996 | Chee et al. |
| 5,549,576 A | 8/1996 | Patterson et al. |
| 5,554,117 A | 9/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,569,182 A | 10/1996 | Twardowski et al. |
| 5,575,769 A | 11/1996 | Vaillancourt |
| 5,607,393 A | 3/1997 | Ensminger et al. |
| 5,613,945 A | 3/1997 | Cai et al. |
| 5,613,974 A | 3/1997 | Andreas et al. |
| 5,614,136 A | 3/1997 | Pepin et al. |
| 5,647,859 A | 7/1997 | Lampropoulos et al. |
| RE35,601 E | 9/1997 | Eckenhoff |
| 5,662,616 A | 9/1997 | Bousquet |
| 5,662,913 A | 9/1997 | Capelli |
| 5,676,656 A | 10/1997 | Brimhall |
| 5,681,289 A | 10/1997 | Wilcox et al. |
| 5,695,490 A | 12/1997 | Flaherty et al. |
| 5,702,363 A | 12/1997 | Flaherty |
| 5,704,915 A | 1/1998 | Melsky et al. |
| 5,713,844 A | 2/1998 | Peyman |
| 5,723,718 A | 3/1998 | Berens |
| 5,725,510 A | 3/1998 | Hartmann et al. |
| 5,741,228 A | 4/1998 | Lambrecht et al. |
| 5,776,096 A | 7/1998 | Fields |
| 5,792,104 A * | 8/1998 | Speckman ........ A61M 39/0208 604/175 |
| 5,792,123 A | 8/1998 | Ensminger |
| 5,797,886 A | 8/1998 | Roth et al. |
| 5,800,414 A | 9/1998 | Cazal |
| 5,810,776 A | 9/1998 | Bacich et al. |

(56) References Cited

U.S. PATENT DOCUMENTS

| | | |
|---|---|---|
| 5,810,789 A | 9/1998 | Powers et al. |
| 5,830,172 A | 11/1998 | Leveen et al. |
| 5,830,196 A | 11/1998 | Hicks |
| 5,833,654 A | 11/1998 | Powers et al. |
| 5,836,935 A | 11/1998 | Ashton et al. |
| 5,840,063 A | 11/1998 | Flaherty |
| 5,876,366 A | 3/1999 | Dykstra et al. |
| 5,879,322 A | 3/1999 | Lattin et al. |
| 5,879,333 A | 3/1999 | Smith |
| 5,879,499 A | 3/1999 | Corvi |
| 5,882,341 A | 3/1999 | Bousquet |
| 5,906,596 A | 5/1999 | Tallarida |
| 5,928,174 A | 7/1999 | Gibbins |
| 5,944,688 A | 8/1999 | Lois |
| 5,951,512 A | 9/1999 | Dalton |
| 5,954,691 A | 9/1999 | Prosl |
| 5,957,890 A | 9/1999 | Mann et al. |
| 5,967,490 A | 10/1999 | Pike |
| 5,989,216 A | 11/1999 | Johnson et al. |
| 6,001,079 A | 12/1999 | Pourchez |
| 6,001,080 A | 12/1999 | Kuracina et al. |
| 6,033,393 A | 3/2000 | Balbierz et al. |
| 6,086,555 A * | 7/2000 | Eliasen ............. A61M 39/0208 604/175 |
| 6,093,180 A | 7/2000 | Elsberry |
| 6,099,508 A | 8/2000 | Bousquet |
| 6,102,884 A | 8/2000 | Squitieri |
| 6,120,492 A | 9/2000 | Finch et al. |
| 6,132,416 A | 10/2000 | Broselow |
| 6,177,522 B1 | 1/2001 | Brady et al. |
| 6,197,845 B1 | 3/2001 | Janssen et al. |
| 6,197,846 B1 | 3/2001 | Combe et al. |
| 6,200,338 B1 | 3/2001 | Solomon et al. |
| 6,213,973 B1 | 4/2001 | Eliasen et al. |
| 6,217,566 B1 | 4/2001 | Ju et al. |
| 6,227,200 B1 | 5/2001 | Crump et al. |
| 6,228,088 B1 | 5/2001 | Miller et al. |
| 6,245,039 B1 | 6/2001 | Brugger et al. |
| 6,280,423 B1 | 8/2001 | Davey et al. |
| 6,355,020 B1 | 3/2002 | Bousquet |
| 6,355,858 B1 | 3/2002 | Gibbins |
| 6,368,658 B1 | 4/2002 | Schwarz et al. |
| 6,375,637 B1 | 4/2002 | Campbell et al. |
| 6,387,105 B1 | 5/2002 | Gifford, III et al. |
| 6,409,700 B1 | 6/2002 | Siegel, Jr. et al. |
| 6,419,643 B1 | 7/2002 | Shimada et al. |
| 6,428,513 B1 | 8/2002 | Abrahamson |
| 6,442,415 B1 | 8/2002 | Bis et al. |
| 6,446,671 B2 | 9/2002 | Armenia et al. |
| 8,574,204 B2 * | 11/2013 | Bourne ................ A61M 39/04 604/288.01 |
| 9,168,365 B2 * | 10/2015 | Bourne ................ A61M 39/04 |
| 2001/0016717 A1 | 8/2001 | Haarala et al. |
| 2001/0056266 A1 | 12/2001 | Tallarida et al. |
| 2002/0082559 A1 | 6/2002 | Chang et al. |
| 2002/0091362 A1 | 7/2002 | Maginot et al. |
| 2002/0138068 A1 | 9/2002 | Watson et al. |

OTHER PUBLICATIONS

Ireland, et al, Safety and Convenience of a Mechanical Injector Pump for Conorary Angiography, Catheterization and Cardiovascular Diagnosis, 1989, 16:199-201.

Miles, et al, Safe use of an Intravenous Power Injector for CT: Experience and Protocol, RSNA, 1990, pp. 69-70.

Carlson, et al, Safety Considerations in the Power Injection of Contrast Media Via Central Venous Catheters During Computed Tomographic Examinations, Investigative Radiology vol. 27, 1992, pp. 337-340.

Steinbach, et al, Breast Implants, Common Complications, and Concurrent Breast Disease, RadioGraphics 1993, 13:95-118.

Vergara, Adverse Reactions to Contrast Media in CT: Effects of Temperature and Ionic Property, Radiology 1996, 199:363-366.

Herts, et al, Power Injection of Contrast Material through Central Venous Catheters for CT: In Vitro Evaluation, Radiology 1996, 200:731-735.

Kaste, et al, Safe Use of Power Injectors with Central and Peripheral Venous Access Devices for Pediatric CT, Pediatr Radiol, 1996, 36:499-501.

Urquiola, et al, Using Lead Foil as a Radiopaque Marker for Computerized Tomography Imaging when Implant Treatment Planning, Journal of Prosthetic Dentistry vol. 77 No. 2, 1997, pp. 227-228.

Hills, et al, Experience with 100 Consecutive Central Venous Access Arm Ports Placed by Interventional Radiologists, JVIR 1997, 8:983-989.

Ruess, et al, In-line Pressures Generated in Small-Bore Central Venous Catheters During Power Injection of CT Contrast Media, Radiology 1997, 203:625-629.

Herzig, et al, The Use of Power Injection with Radiographic Contrast Media Into PICC Lines, JVIR, vol. 11 Issue 2 Supp. pp. 1-535.

Blot, et al, Accuracy of Totally Implanted ports, tunnelled, single and multiple-lumen contral venous catheters for measurement of central venous pressure, Intensive Care Med, 2000, pp. 1837-1842.

Herts, et al, Power Injection of Contrast Media Using CVC: Feasibility, Safety, and Efficacy, AJR: 176, pp. 447-453.

Biffi, et al, A Randomized, Prospective Trial of Central Venous Ports Connected to Standard Open-Ended or Groshong Catheters in Adult Oncology Patients, American Cancer Society, 2001, pp. 1204-1212.

User Manual for the ESPrit 3G Speech Processor and Accessories, Nucleus Cochlear Implant Systems.

Salis, et al, Can PICC be Used for Contrast Injection with a CT Power Injector, JVIR vol. 13, Issue 2, Supp S1-S117.

Funaki, Central Venous Access: A Primer for the Diagnostic Radiologist, AJR: 179, 2002, pp. 309-318.

* cited by examiner

IMPLANTABLE MEDICAL DEVICE FOR IMPROVED PLACEMENT AND ADHERENCE IN THE BODY

FIELD OF THE INVENTION

This invention relates generally to implanted medical devices used to access subcutaneous regions within a body, such as vasculature.

BACKGROUND OF THE INVENTION

Long term access to a patient's body is required for many medical treatments including antibiotic therapy, hemodialysis access, chemotherapy regimens, and other treatments that require repeated administration, withdrawal, or exchange of fluids. In some cases, internal access to the patient is required for years.

Subcutaneously implanted access ports are one type of medical device that can be used for this purpose. These medical devices often either include or are attached to a catheter used for the administration, withdrawal, and/or exchange of fluids from the patient. A pocket is made in the subcutaneous tissue, and the medic device is placed into the pocket.

Access ports generally have a molded or rigid housing, with a fixed number of suture holes. These suture holes protrude from the housing of the medical device, causing it to have a larger overall size than it otherwise would have. During implantation, a physician is thus required to create an incision in the body of sufficient size to allow insertion of the device. Further, rigid appendages on the housing of the medical device can make manipulation of the device within the body of a patient difficult for a physician.

Suturing of such a device can be performed by the physician to secure or stabilize the device. A number of factors determine whether or not the medical device is sutured in place, including the pocket configuration, the type of training received by the physician, and the physician's preference. Once the device is properly positioned and secured, the pocket is closed.

There is a wide range of preferences among physicians regarding the number and location of suture holes. Some physicians prefer one, two, three, four, or more suture holes. Some physicians prefer not to have any suture holes, and yet others prefer to have any suture holes that are present filled with a material such as silicone to minimize fibrin ingrowth into the suture holes, thereby facilitating subsequent removal of the device.

After suturing has been completed, the rigid housing of the medical device and the associated suture holes do not readily accommodate movement of the patient. Movement of the patient causes the tissue to which the medical device has been sutured to move. The rigidity of the device thus results in increased tension on the sutures, resulting in discomfort and irritation to the patient.

SUMMARY OF THE INVENTION

In one aspect, the invention features an implantable medical device for percutaneous access to a body comprising a flexible member and a housing defining an entry site for the administration, withdrawal, or exchange of fluids. The flexible member is attached to a surface of the housing and stabilizes placement of the medical device within the body. An adhesive is disposed on a first surface of the flexible member and attaches the flexible member to the housing surface. The flexible member can comprise suture locations, and the suture locations can define one or more suture holes. The suture holes can be filled with a material to minimize tissue ingrowth, such as fibrin. The material can be silicone or a biocompatible polymer, and is preferably penetrable by a suture needle.

The flexible member can have a perimeter region penetrable by a suture needle, which can be formed of materials including polyurethane, thermoplastics, elastomers, and fiber reinforced elastomers. The flexible member can also include tabs, which can be located about a perimeter of the flexible member. The tabs can define one or more suture holes.

The flexible member can be coated with a tissue growth substance and can be shaped and/or textured to conform to tissue within the body. A second surface of the flexible member can include an adhesive for attaching the device to tissue within the body. The flexible member can be preformed to mate with the housing. It can also be shaped to surround a perimeter of the housing.

Another aspect of the invention features a flexible member for stabilizing the placement of a medical device within a body. The flexible member includes a flexible substrate that mates with the medical device, one or more suture locations formed on the flexible substrate, and an adhesive. The flexible member can be formed from a material penetrable by a suture needle. Materials such as polyurethanes, thermoplastics, elastomers, and fiber-reinforced elastomers can be used to form the flexible member.

The flexible member can comprise one or more suture locations, and these can each define one or more suture holes. The suture holes can be filled with a tissue growth substance that inhibits tissue growth. The suture holes can be filled with substances such as silicone and biocompatible polymers. In one embodiment, the substance is penetrable by a suture needle.

The flexible member can also include tabs, and the tabs can be disposed about the perimeter of the flexible member. The tabs can be flexible and can be penetrable by a suture needle. The flexible member can be coated with a substance to inhibit tissue growth. It can also be preformed to mate with the perimeter of a surface of the medical device and can have a second surface shaped to conform to subcutaneous tissue within the body.

At least a portion of the perimeter of the flexible member can follow a perimeter of the surface of the medical device to which the flexible member is attached. The flexible member can include an adhesive to secure the flexible member to the medical device. The adhesive, can include methoxy-perfluoropropane, thixotropic sealants, and water-based adhesives.

Another aspect of the invention features a method of manufacturing an implantable medical device that comprises providing a housing defining an entry site for the administration, withdrawal, or exchange of fluids, and attaching a flexible member thereto, for stabilizing placement of the housing within the body. The flexible member can be formed by cutting a sheet of polymer. The method can include applying an adhesive to the flexible member by at least one of spray coating, slot coating, spiral spraying, melt-blowing, pattern coating, layering, dipping and drying, and ion deposition.

Another aspect of the invention features a method of fabricating a flexible member which includes forming a shape for mating with an implantable medical device, forming suture locations about the shape of the flexible member, and applying an adhesive to the shape. The shape can be formed by cutting from a sheet of polymer, and suture holes can be formed in the flexible member.

BRIEF DESCRIPTION OF THE DRAWINGS

These and other features of the invention are more fully described below in the detailed description and accompanying drawings of which the figures illustrate an apparatus and method for securing an implantable medical device within a body.

DETAILED DESCRIPTION

Figure 1:
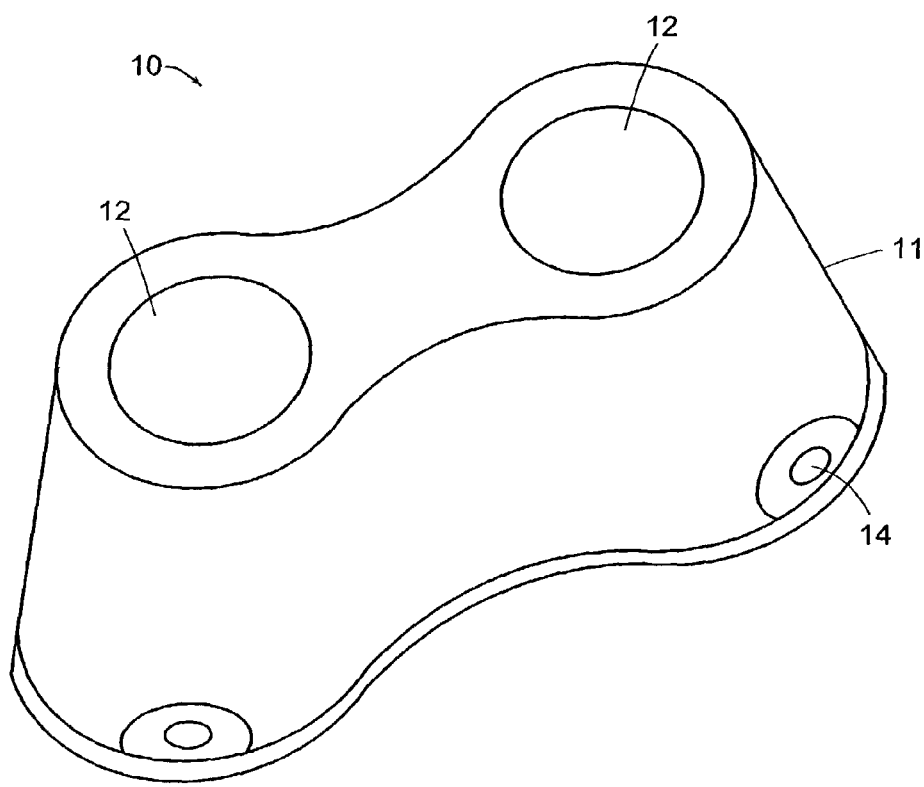
FIG. 1 illustrates a prior art device used to provide access to provide access to subcutaneous regions within a body, such as vasculature.

FIG. 1 shows a prior art access port used by a physician to provide access to subcutaneous regions within the body, such as vascallature. The medical device 10 includes a housing 11 and an entry site 12 for the administration, withdrawal, or exchange of fluids. The entry site can be a septum. The needle of a syringe, for example, can be used to administer or withdraw fluids through the septum. The medical device can be surgically implanted beneath the skin of a patient.

The medical device can also include a predetermined number of suture holes 14 disposed about the base of the housing in fixed locations. The suture holes can be molded into the housing 11 as shown. A physician can tie a suture through the suture hole, thus securing the medical device 10, for example, to adjacent tissue. The medical device shown has two entry sites 12.

Figure 2:
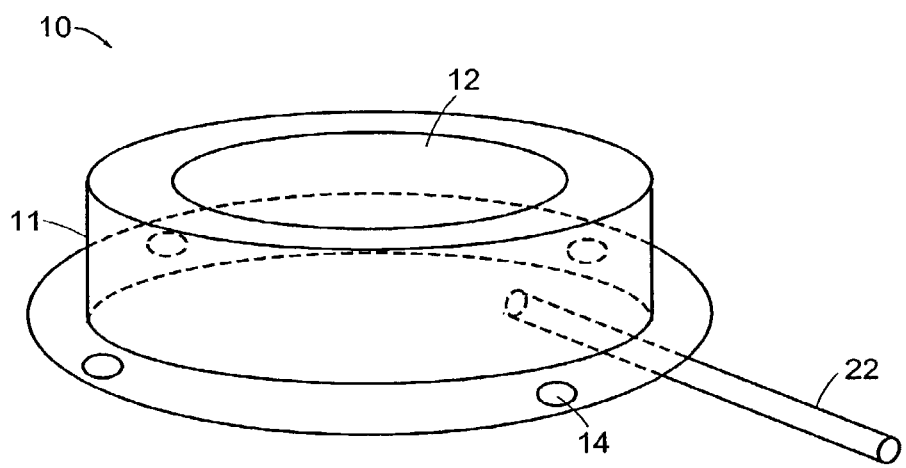
FIG. 2 illustrates another prior art device with only one entry site.

FIG. 2 illustrates another prior art access port with a single entry site 12. A catheter 22 is attached to the medical device 10. Suture holes 14 are disposed about the base of the housing 11 at fixed locations.

Figure 3:
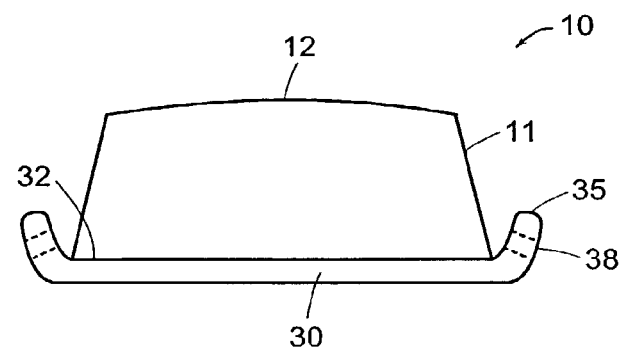
FIG. 3 illustrates a side elevation view of an embodiment of the invention.

FIG. 3 is an illustration of an embodiment of an access port incorporating principles of the invention. The medical device 10 comprises housing 11 and an entry site 12. The shape of the housing 11 defines the entry site 12, as shown.

The entry site is used to administer, withdraw, or exchange fluids with a body, and can comprise a septum. A physician can penetrate the septum with the needle of a syringe.

A flexible member 30 is attached to a surface 32 of the housing. A perimeter region 35 of the member 30 is non-rigid and flexible. When flexed, the size of the incision required for insertion of the medical device in a body can be reduced. Suture locations 38 are disposed along the perimeter region 35 of the flexible member 30.

Figure 4:
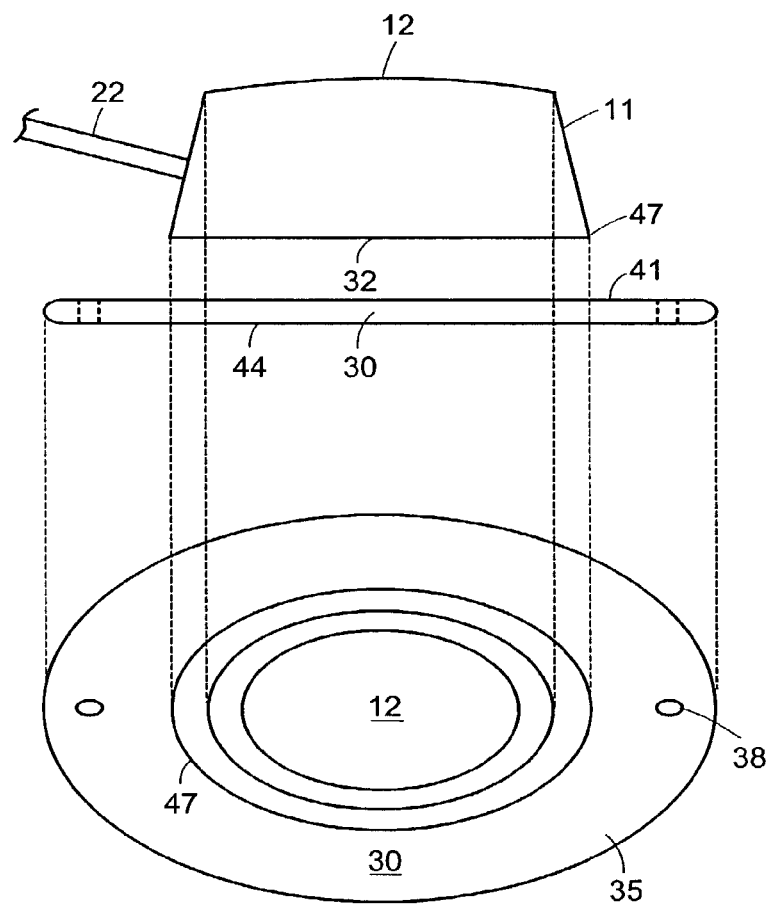
FIG. 4 illustrates a side and top view of another embodiment of the invention.

FIG. 4 illustrates a flexible member 30 having a first surface 41 and a second surface 44. The first surface 41 comprises an adhesive, which allows the flexible member to be attached to the surface of the housing 32. In one embodiment, the flexible member is preformed tape, having an adhesive surface that easily adheres to the surface of the housing 32. The tape can take various shapes, forms, thicknesses, and orientations. The flexible member 30 can be attached to the housing surface 32 before surgery. Adhesively attaching the flexible member 30 to housing surface 32 of medical device 10 allows a physician to implant the medical device within a body us rig an incision of reduced size. Alternatively, the flexible member can be attached to the housing surf ice after implantation into a body. This is accomplished by attaching the flexible member 30 to the housing 32 after each has been inserted into the body through the incision. In this embodiment, the incision size can be reduced still further.

The flexibility of the member 30 also enhances the manipulation and placement attributes of the device, providing a physician with increased capabilities and reducing aggravation and irritation to a patient. Patient recovery and comfort are thus enhanced. The flexible member also results in improved comfort and reduced irritation to the patient after the medical device has been implanted. Movement of a patient causes the tissue to which the medical device has been sutured to move. The resiliency of the flexible member thus reduces the stress to the body tissues of the patient during movement of the patient. This results in reduced irritation to the body and increased patient comfort. If sutures are present (discussed below), the benefit of this feature is increased.

The perimeter region 35 of the flexible member 30 can extend beyond the perimeter 47 of the housing surface. As shown, the perimeter region 35 of the flexible member 30 can extend beyond the perimeter of the housing surface 47 on all sides. In other embodiments, the perimeter region 35 can extend beyond the perimeter 47 of the housing surface on fewer than all sides.

Figure 5:
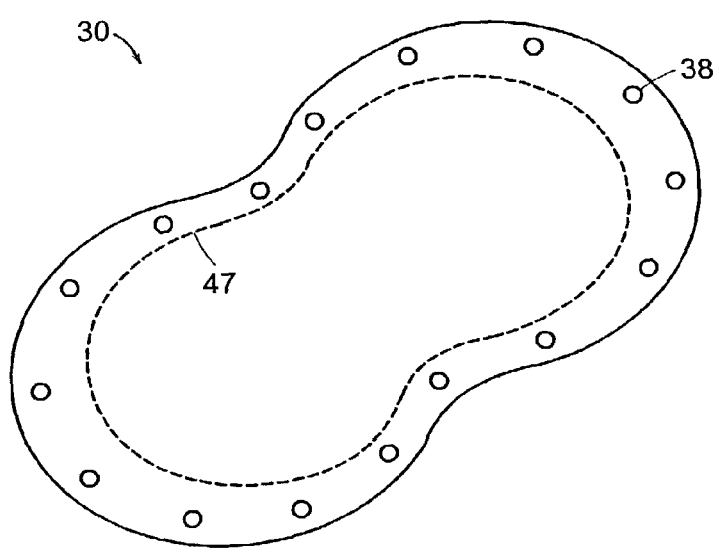
FIGS. 5-8 are a top view of other embodiments of the invention.
Figure 6:
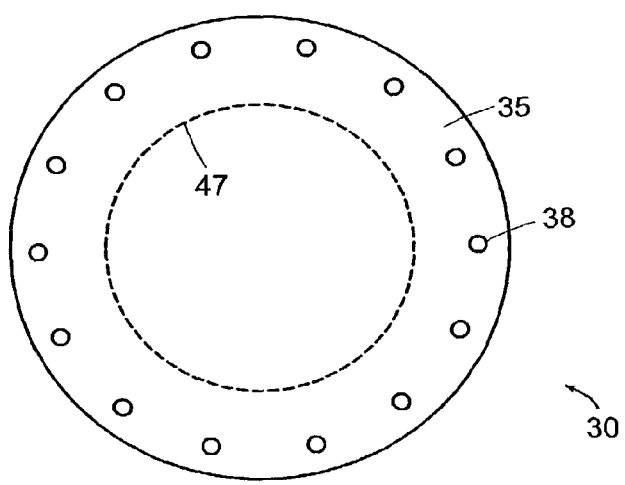

FIGS. 5-8 show a top view of different embodiments of the invention. FIGS. 5 and 6 illustrate a flexible member comprising a perimeter region 35. This perimeter region 35 can extend beyond the perimeter of the housing surface 47 when the flexible member is attached to surface 32 of housing 11. The perimeter region 35 ran extend beyond the housing perimeter 47 in all directions, as shown. In other embodiments, it extends beyond the housing perimeter 47 in fewer directions. In any of these embodiments, a plurality of suture locations 38 can be disposed about the perimeter region 35 of the flexible member 30.

Figure 7:
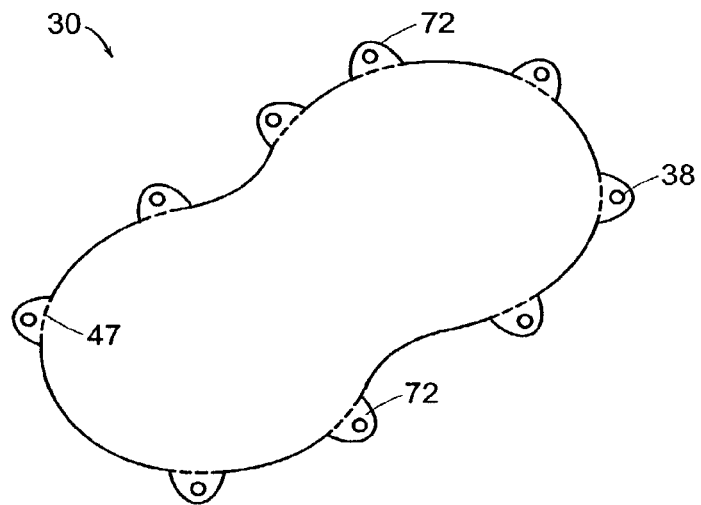
Figure 8:
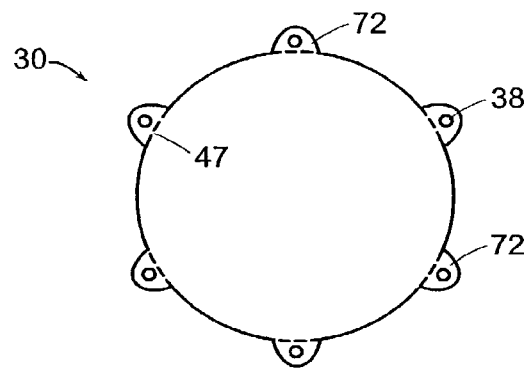

FIGS. 7 and 8 illustrate flexible members 30 comprising preformed tabs 72 that extend beyond the perimeter of the housing surface 47. Each of these tabs 72 can include one or more suture locations 38.

Each of the embodiments found in FIGS. 5-8 can be formed as a preformed flexible member. The shapes illustrated in these figures are intended to conform generally to the perimeter of the housing surface 47 to which they can be attached. In other embodiments, however, the flexible member may not cot form to the perimeter of the housing.

Figure 9:
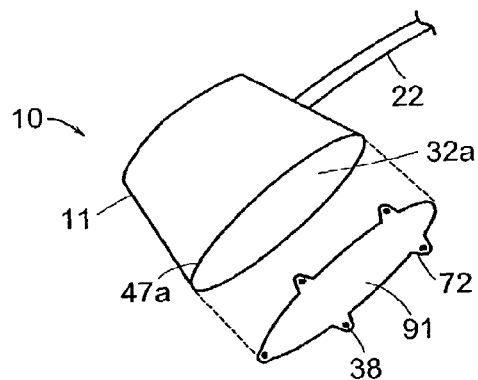
FIGS. 9 and 10 are perspective views that show different ways the flexible member can be attached to a surface of a medical device.

FIG. 9 illustrates the manner in which an embodiment of the flexible member 91 can be joined with the housing surface 32A of medical device 10. Tabs 72 comprising suture locations 38 extend beyond the perimeter of the housing surface 47A providing locations to which a suture can be conveniently attached.

Figure 10:
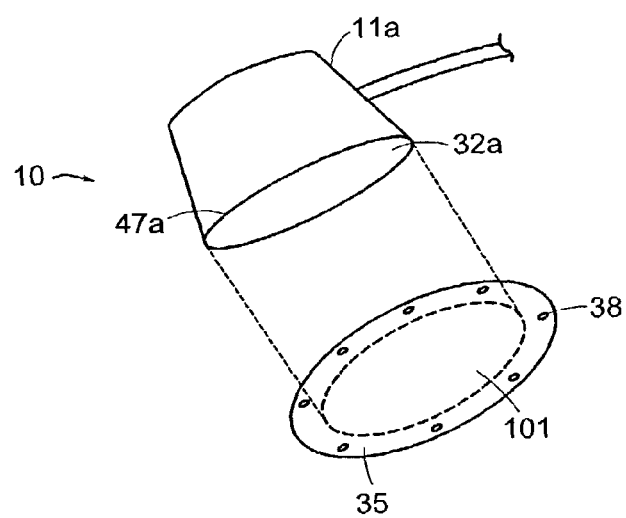

FIG. 10 illustrates a perspective view of another embodiment of a flexible member 101 that can be joined with the housing surface 32A of medical device 10. In this embodiment, the perimeter region 35 comprises suture locations 38 and extends beyond the perimeter of the housing surface 47A. As shown in FIGS. 9 and 10, both embodiments of the flexible member (91, 101) can be effectively attached to housing surface 32A and efficiently mate with the perimeter 47A of the housing surface. When attached to the housing surface 32A, both embodiments (91 and 101) of the flexible member adhere to the entire housing surface 32A, in other embodiments, this may not be required. Rather, the flexible member can be shaped to adhere to only a portion of the housing surface. This is useful if it is necessary to stabilize only a portion of the medical device.

Figure 11:
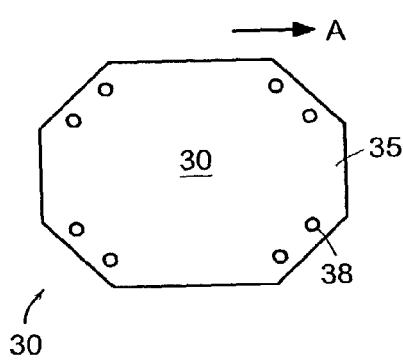
FIGS. 11-14 are top views illustrating additional embodiments of the invention.

FIG. 11 illustrates an asymmetrical embodiment of the invention. In particular, the perimeter region 35 extends further in the direction labeled as "A" than in the other directions. Thus, the dimension of the perimeter region 35 of the flexible member 30 is larger in direction A than in the other direction shown. This embodiment includes a plurality of suture locations disposed in the perimeter region 35. The presence, location, and number of suture locations are determined by the needs and preferences of the physician using the device.

Figure 12:
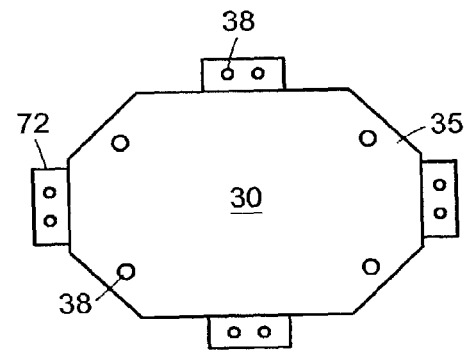

FIG. 12 illustrates an embodiment of the flexible member 30 comprising suture locations 38 disposed both in a perimeter region 35 and on tabs 72. It is not necessary for all or any of the suture locations 38 to be sutured by a physician. This embodiment also illustrates that more than one suture location 38 can be present on a tab 72.

Figure 13:
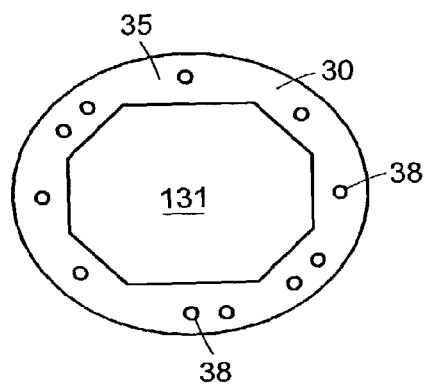

FIG. 13 illustrates an embodiment of the flexible member 30 comprising a hole 131 in the center of the flexible member. Further, the suture locations 38 are asymmetrically disposed about the perimeter region 35 of the flexible member 30. This and other embodiments of a flexible member can be used to fulfill customized surgical requirements.

Figure 14:
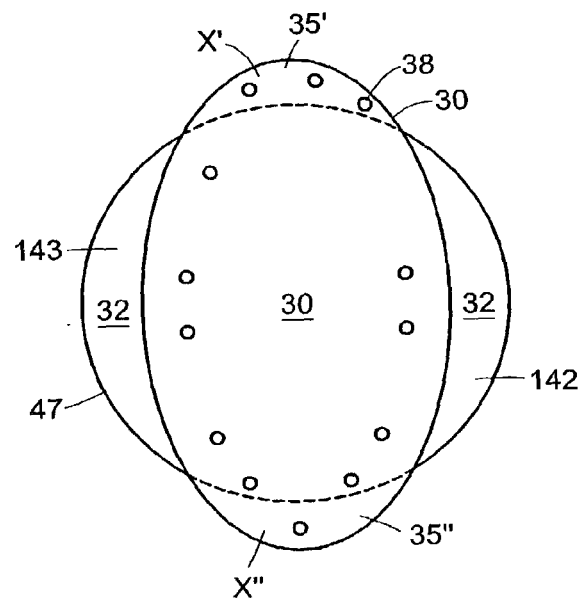

FIG. 14 illustrates a bottom view of an embodiment in which the flexible member 30 extends beyond the perimeter of the housing surface 47 at two areas, labeled as X' and X" on the figure. Suture locations 38 are present at perimeter regions 35' and 35". As shown, portions of the housing surface 32 are not in contact with the flexible member 30. A physician can also use this embodiment to meet varying surgical requirements and preferences. For example, in this embodiment exposed housing surfaces 142 and 143 are not in contact with flexible member 30. Thus, a physician can grasp these surfaces directly and use them to manipulate the medical device during implantation of the medical device into a body. The desirability and utilization of this and other specific embodiments of the invention varies widely among physicians.

Figure 15:
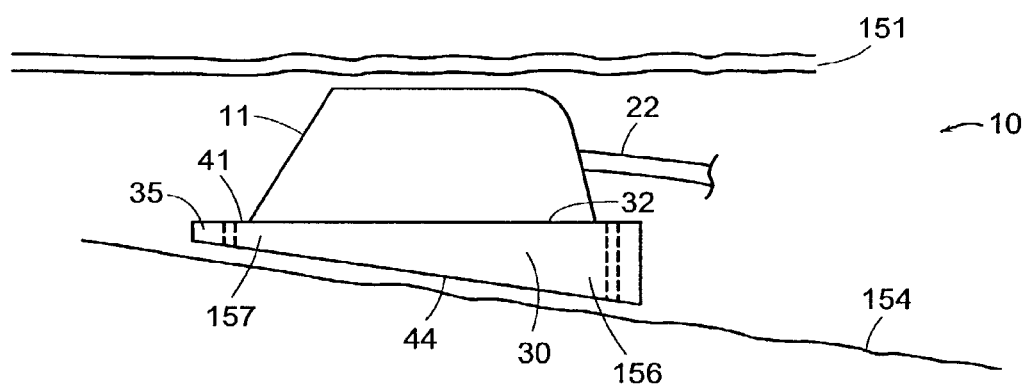
FIG. 15 is a side view of a flexible member shaped to conform to tissue within the body.

FIGS. 15-18 illustrate various thickness characteristics of the flexible member 30 of the invention. Each of these embodiments can include tabs 72 and perimeter regions 35. In FIG. 15, the thickness of the flexible member 30 varies along us length. The medical device. 10 is illustrated as being surgically positioned between a cutaneous layer 151 and a tissue layer 154. The flexible member 30 includes a region of increased thickness 156 and a region of lower thickness 157. The varying thickness of the flexible member allows it to fit snugly between the surface of the housing 32 and the tissue layer 154. As shown, the contour of the second surface 44 of the flexible member is shaped to conform to the shape of the tissue layer 154. Although the first surface 41 of the flexible member can also be contoured, this is not necessary in all embodiments.

Figure 16:
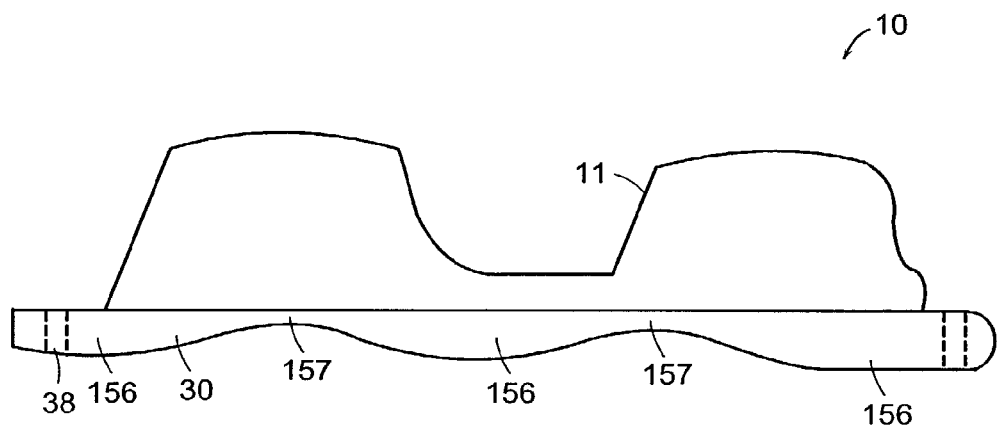
FIG. 16 is a side view of a flexible member that is preformed to mate with a medical device.

FIG. 16 illustrates a flexible member 30 having a non-uniform variation in its thickness. Thickness variations such as these are used to match the shape of muscle, other tissue formed within the body, and the like. This feature can used to improve the placement stability of the medical device within a body.

Figure 17:
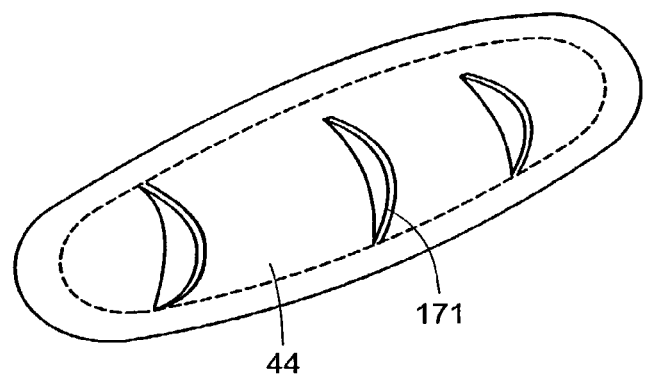
FIGS. 17-18 illustrate embodiments of the invention with different thickness characteristics.

FIG. 17 illustrates a bottom view of yet another embodiment in which the second surface of the flexible member 44 comprises ridges 171 for stabilizing placement of the medical device 10. Ridges such as these are useful for preventing longitudinal motion of the flexible member when in contact with the body tissue.

Figure 18:
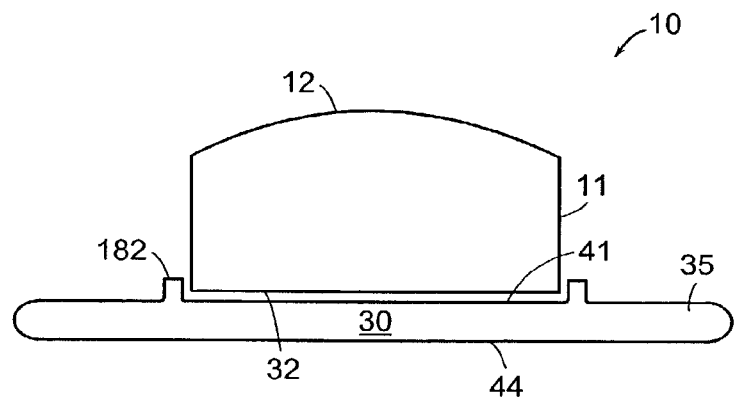

Referring to FIG. 18, the shape of the flexible member can be preformed to mate with a perimeter of the medical device. The flexible member 30 comprises extensions 182 that are formed to mate with the surface of the housing 32, and are positioned at points about the perimeter 47 of the housing surface. In one embodiment, these extensions 182 form a continuous ridge on the first surface 41 of the flexible member, encircling the perimeter 47 of housing surface 32 and facilitating accurate alignment with the housing 11. The first surface 41 can be coated with an adhesive to facilitate attachment to the surface of the housing 32.

Figure 19:
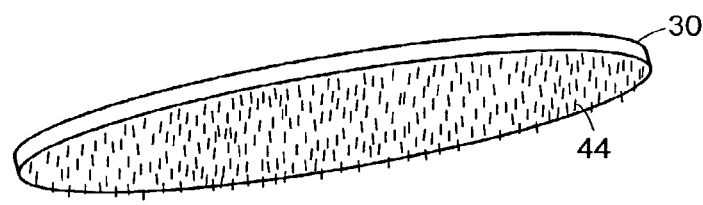
FIGS. 19 and 20 each illustrate an embodiment of the invention with different surface textures.
Figure 20:
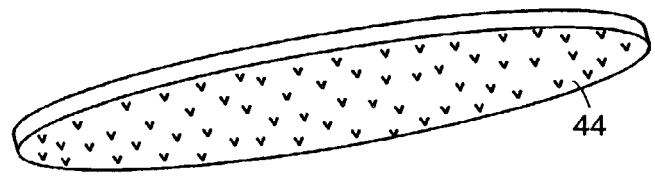

FIGS. 19 and 20 illustrate embodiments comprising a second surface 44 of the flexible member with different textures. These textures can include, for example, bumps or hair-like tentacles. These textures canoe unidirectional (as shown in FIG. 20) or can be oriented in multiple directions. Textures can be formed as an integral part of the flexible member, or they can be attached to a surface of the flexible member after it has been formed. Although FIGS. 19 and 20 show the entire second surface 44 of the flexible member covered with a texture, in some embodiments only a portion of the second surface 44 is covered. Moreover, combinations of the different types of textures can be used on the same flexible member. The first surface 41 of the flexible member can also have a texture, although a smooth surface is generally preferred to promote more effective adhesion with the housing surface 32.

The suture locations 38 can be an important element of some embodiments of the invention. In one embodiment, the suture locations 38 comprise permeable portions of the perimeter region 35 of the flexible member 30, such as a permeable membrane. For example, the suture locations in each of the embodiments described above comprising a perimeter region 35 can have one or more suture locations 38 including a permeable membrane. A permeable membrane is any biocompatible material that a physician can penetrate with a suture needle, either before or during implantation of the medical device within the body of a patient. A perimeter region 35 can comprise zero, one, or a plurality, of suture locations. Furthermore, in some embodiments the entire perimeter region 35 can be penetrable by a suture needle, and thus can function as a large suture location 38. In still other embodiments, the entire flexible member 30 can be penetrable by a suture needle.

For embodiments comprising a permeable membrane, the suture location 38 is generally made of as material that closes back about the suture or suture needle after the material has been penetrated. Suture locations such as these can be penetrated one time or multiple times by a suture needle. Generally, a physician penetrates a given point within a suture location only once with a suture needle, although the same point on a suture location can be penetrated multiple times. However, a suture location can readily be sutured multiple times by a physician if multiple sutures are to be attached to that suture location, and these sutures can be positioned at the same or different points. The suture location thus comprises a permeable membrane that can be penetrated at multiple different locations. Multiple sutures can thus be located adjacent to each other, can be scattered about the suture location 38, or can be scattered about the perimeter region 35, all at the discretion of the physician. This is a useful feature in that a physician does not have to determine before surgery if, or how many, sutures are needed, or precisely at what locations about the medical device 10 they will be placed.

The decision to attach any sutures to the medical device at all is at the discretion of the physician. Stabilization of the placement of the medical device 10 within a body using the flexible member 30, without suturing, and either with or without the presence of suture locations, represents a preferred embodiment for some physicians.

In other embodiments, suture holes 14 may be punched into suture locations 38. Suture locations 38 in each of the embodiments described above can have one or more suture holes 14. The use of suture holes 14 eliminates the need for a physician to force a suture needle through the material of the suture location 38. More than one hole may be located in a suture, location, and suture holes can be conveniently punched into the flexible member 30 before surgery using simple tools. Alternatively, suture holes 14 can be preformed at suture locations 38 about the perimeter region 35 of flexible member 30 at the time of manufacture.

In some embodiments prepunched patterns are formed, for example, in the perimeter region 35 or on the tabs 72 of the flexible member 30 to facilitate the creation of suture holes 14. Holes prepunched in this manner each have an easily removable plug, the removal of which creates suture holes 14 ready for use by a physician.

Although reference to sutures, suturing, and suture needles has been made above, the invention is equally applicable to staples, hooks, and other devices and means known to those of skill in the art for placing, securing, or attaching devices within a body. Use of the terms suture and suturing is intended to include these other devices and methods.

Furthermore, the above discussion has centered on suture locations 38 disposed within the perimeter region 35 specifically, and generally within the flexible member 30. However, the invention also includes suture locations 38 disposed within tabs 72, as discussed above. These suture locations can include suture holes 14, or not. As with the flexible member 30 and the flexible region 35, these tabs are preferably foldable and flexible.

In embodiments, the suture holes 14 can be filled with a filling material. This filling material can be added to the suture hole 14 before surgery, and preferably during manufacture of the flexible member 30. The filling material should be formed of a soft material such as silicone that can be penetrated by a suture needle, and that will close about a suture after suturing. Other materials can be used to fill the suture holes 14, such as CORETHANE® (registered mark of Corvita Corporation, Miami, Fla.), polyurethane, and bionate polycarbonate urethanes. Materials with a Durometer reading of 50-55 are preferred for this purpose. Such materials are relatively soft, and can be conveniently punctured with a needle. An appropriate material thickness should be used, as is apparent to one of ordinary skill in the art. The suture holes 14 can be filled or pre-filled with the filling material. The presence of the filling material in the suture hole 14 minimizes tissue ingrowth into the suture hole, making subsequent removal of the medical device less difficult.

Additionally the flexible member 30, and the medical device, can be coated with a material, for example, to inhibit tissue ingrowth. Suitable coatings include but are not limited to antimicrobial coatings for the prevention of microbial biofilming, hydrogel coatings, zinc oxide coatings for preventing surface irritation, various block copolymers, tackifying resins, and polybutene. The medical device and the flexible member can also be impregnated with an antimicrobial substance, preferably at least in a portion of the device that will be located near the cutaneous layer 151.

Figure 21:
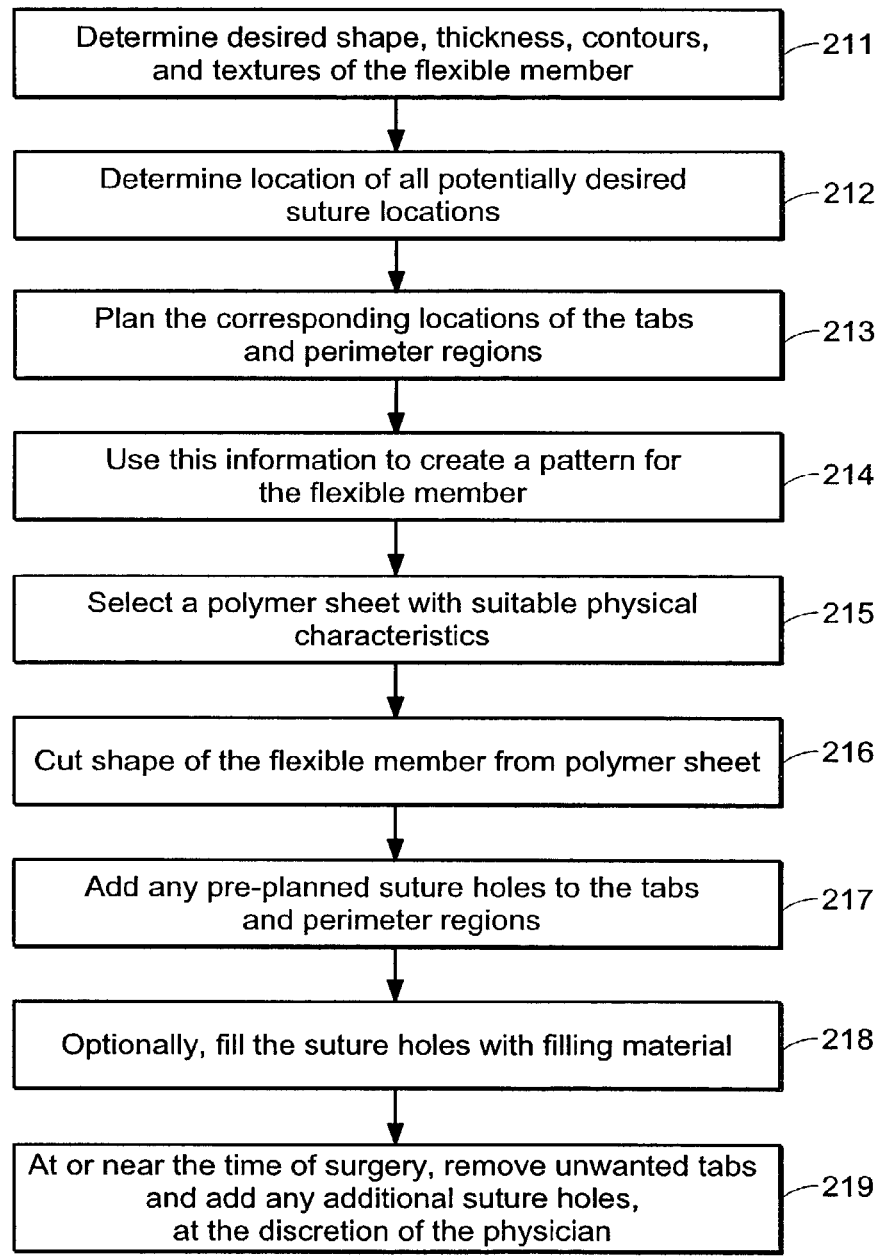
FIG. 21 is a flow chart illustrating steps that can be used to manufacture a flexible member of the invention.

FIG. 21 is a flow chart illustrating steps that can be used to manufacture a flexible member. First the desired shape, thickness, contours, and textures of the flexible member are determined (step 211). The locations of all the desired suture locations 38 are next determined (step 212). Which suture locations 38 will comprise tabs 72 and which will comprise perimeter regions 35 is next determined. Since tabs can easily be removed later, additional tabs can be included that perhaps might not be used during implantation of the device. A pattern can be created for the flexible member (step 214) and a suitable polymer sheet selected (step 215). Preferably, the thickness regions 156, 157, extensions 182, surface textures, and contours of the flexible member are achieved by selecting a polymer sheet possessing the desired characteristics.

A shape corresponding to the pattern can then be cut from a polymer sheet (step 216), such as silicone. Any preplanned suture holes 14 can next be added to the tabs 72 and the perimeter regions 35 (step 217). These, can be added, for example, by puncturing. Optionally, any suture holes 14 that have been tanned in step 217 can be filled with a substance to inhibit tissue growth into the suture hole (step 218). Finally, at the discretion of the physician, additional suture holes can be added to suture locations 38 and any unwanted tabs 72 can be severed from the flexible member, at the time of surgery (step 219).

To complete the manufacture of a medical device, a housing, such as that of an implantable port, is provided. The flexible member is then attached to a surface of the medical device. When implanted within the body, the medical device exhibits improved placement stability.

Other embodiments of the manufacturing process are also possible. For example, an adhesive coating can be applied to the flexible member after it has been cut from the polymer sheet, or the polymer sheet can comprise an adhesive material before the cutting is performed. Preferably, the adhesive is applied to the sheet of polymer material by at least one of slot coating, spiral spraying, melt blowing, pattern coating, layering, dipping/drying, and ion deposition.

Suitable biocompatible adhesives are known to those of ordinary skill in the art, and include water-based adhesives, methoxy-perfluoropropane, and thixotropic sealants. Such adhesives can be coated continuously or discontinuously, and are compatible with muscle, tissue, skin surfaces, and the like. The first surface 41 of the flexible member comprises such an adhesive, for contacting the housing surface 32. Optionally, the same or a different adhesive can be applied to the second surface 44 of the flexible member, for contacting tissue layer 154. Tissue-specific adhesives can also be used. The application of adhesive to tie second surface 44 of the flexible member contributes to the placement stabilization of the medical device 10. Adhesives of low or moderate tacking strength can also be used on either surface, to facilitate repositioning or removal of the flexible member. Preferably, the adhesive selected for this purpose will not leave a residue or exhibit any adhesive transfer to the tissue surface 154 upon removal or relocation of the medical device 10. Materials left behind after removal of the medical device can adversely affect healing of the body.

The flexible member 30 can be manufactured from many different materials. Preferably, the flexible member is formed from at least one of thermoplastics, elastomers, polyurethanes, and fiber reinforced elastomers. Suitable fibers for this purpose include polyester or Kevlar® fiber. Kevlar® is a registered trademark of E.I. duPont de Nemours and Company. The flexible member can also be manufactured from materials such as a latex/plastic polymer blend, silicone, vinyl, foam, rubbers, varying percentages of rubbery block co-polymers and midblocks comprising ethylene/propylene and ethylene/butylene, and mixtures thereof, S-EP block co-polymers (styrene-ethylene/propylene), dycyclopentadiene, fully hydrogenated aliphatic C5 and C9 resins, and alpha-methylstyrene based resins.

Various packaging and usage options are within the scope of the invention. For example, a package can be sold that includes a set of pre-cut flexible members or "frames." The physician can then select the desired style from the set, attach it to the medical device, and perform the implantation. The package can include flexible members with, for example, a one, two or three-hole option. The physician merely selects the flexible member that meets his needs and preferences. Optionally, if desired, the medical device can be trimmed and/or suture holes can be added, before attaching a flexible member.

Figure 22:
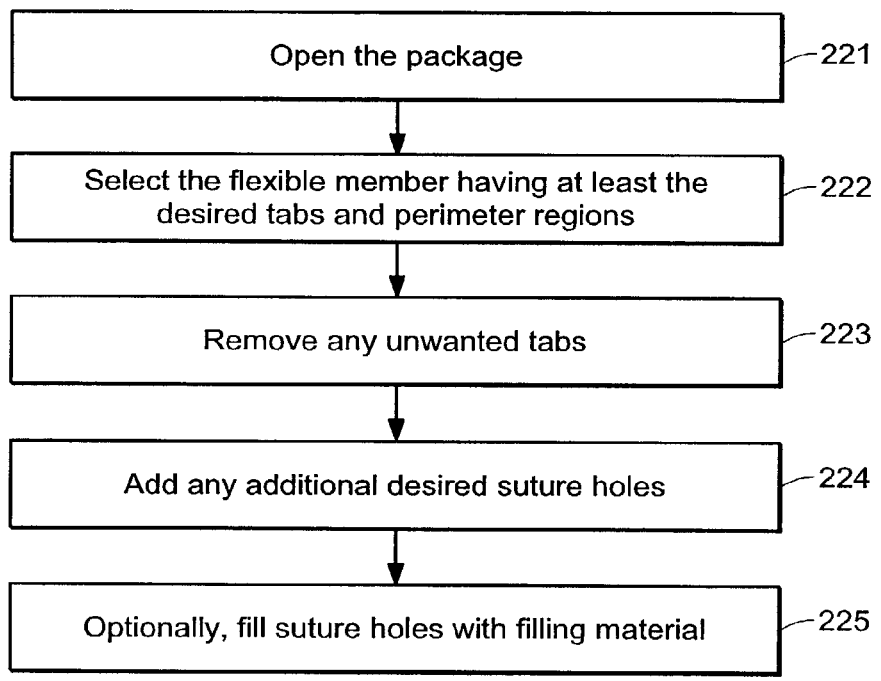
FIG. 22 is a flow chart illustrating steps that can be used by a physician to prepare the flexible member for use.

FIG. 22 is a flow chart illustrating steps that can be used by a physician to select and prepare the flexible member for use. A physician opens a package containing a number of flexible members (step 221). One of the flexible members from the package is selected. The flexible member selected should have tabs 72 and perimeter regions 35 in at least each of the locations desired (step 222). Extra, unwanted tabs can be removed by cutting (step 223). Any additional suture holes 14 can be added (step 224), for example, by puncturing. Optionally, a filling material such as silicone can be added to any suture holes that have not been prefilled, to prevent or minimize tissue ingrowth. These unfilled suture holes can be filled by the physician or his staff before surgery, or after implantation into the body of a patient (described below). The unfilled suture holes could have been formed, for example, in either step 224 or step 217.

Figure 23:
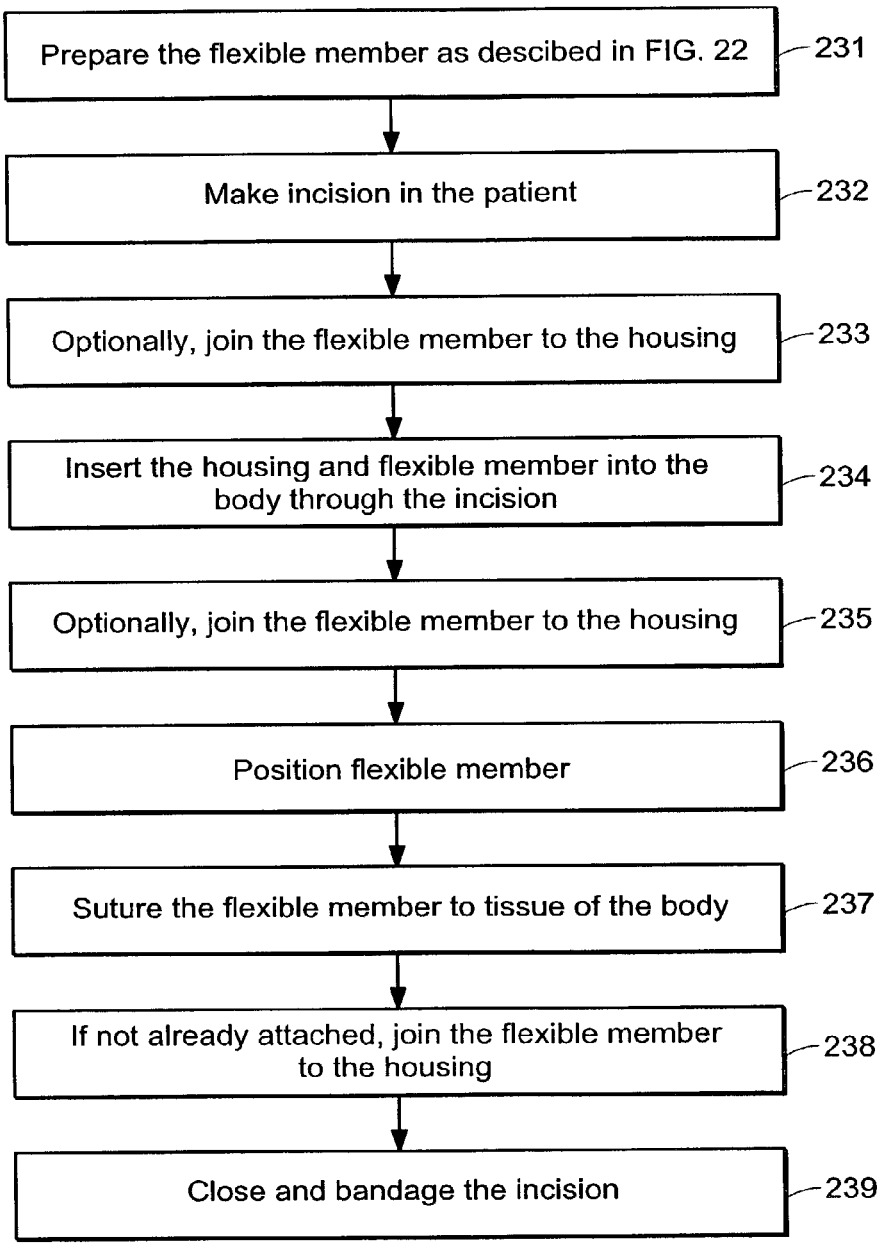
FIG. 23 is a flow chart illustrating steps that can be used to implant a medical device of the invention.

FIG. 23 is a flow chart illustrating steps that can be used to implant and secure a medical device 10 comprising a flexible member 30 into a body. Various methods can be used for this purpose. The physician first determines the location and number of suture locations desired and prepares the flexible member as described in FIG. 22 (step 231). If the flexible member has tabs 72, any undesired tabs are removed. If insufficient suture holes 14 are present, more can be added by puncturing the appropriate suture location(s) of the flexible member. More than one suture hole can be added to each suture location, depending upon the physician's preference.

A linear incision is made in the patient (step 232). The incision is of reduced size, due to the planned usage of the flexible member. The flexible member can be adhesively attached to the housing surface 32 at this time (step 233), or it can be attached later. Attaching it later allows the smallest incision size to be used.

The housing 11 and the flexible member 30 are inserted through the incision, into the body of the patient, near an area in which the catheter 22 is to be placed. The physical positions the catheter, and then positions the flexible member adjacent the tissue layer 154 (step 236). The flexible member is then sutured into place (step 237). This can be done by sewing subcutaneous sutures through the suture locations 38, thereby securing the flexible member 30 to adjacent tissue. The flexible member is now attached to the housing surface 32, if it has not already been attached (step 238). The incision is then closed and bandaged (step 239).

The sutures can thus be used to anchor the tissue layer 154 and/or the cutaneous layer 151 to the medical device 10. In other embodiments tissue can be anchored the medical device using subcutaneous hooks and other devices and methods known to the skilled artisan.

In some embodiments the flexible member 30 or the housing 11 can be coated with materials that promote tissue growth to provide better sealing of the incision, such as collagen or other tissue growth catalysts and substances. Materials that promote ingrowth of cells, such as a permeable fabric, a textured polymer, or appropriate mesh materials can also be bonded to or embedded into the surface of medical device 10. The added ingrowth materials cause the skin surrounding the medical device 10 to bond securely with the medical device 10. Alternatively, growth inhibition materials can be placed on or around the medical device. For example, suture holes 14 that will not be used can be filled with silicone to prevent tissue ingrowth. Thus, fibrin will not grow into these suture locations, and the medical device can later be more easily removed.

The flexible member of the invention is suitable for use with various medical devices including implantable venous ports, PEG ports, and other epidermal and indwelling medical devices that, for example, provide access to the body or to vasculature. These include devices used for gastrointestinal feeding and metering, intervascular pumps, insulin pumps, drainage products (such as for draining an abscess), pacing products (such as pacemakers), and various catheters.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An implantable port for fluid access to a target site within a body, said implantable port comprising:
    a housing defining an entry site comprising a septum formed therein for the administration, withdrawal or exchange of fluids with the target site, the housing having a side wall extending from the entry site to a base;
    a needle-penetrable region adjacent to and spanning a majority of a perimeter of said implantable port, wherein the needle-penetrable region comprises a needle-penetrable material configured to allow complete penetration by a suture needle to attach a suture, and the needle-penetrable material extending from the base along the side wall for a selected distance.

2. The implantable port of claim 1, wherein the needle-penetrable material extends below the base.

3. The implantable port of claim 1, wherein the needle-penetrable material is flush with the base.

4. The implantable port of claim 1, wherein the needle-penetrable region is devoid of any preformed spaces not containing the needle-penetrable material between the housing and the base.

5. The implantable port of claim 1, wherein the needle-penetrable material comprises a flexible polymer.

6. An implantable port for fluid access to a target site within a body, said implantable port comprising:
- a housing defining an entry site comprising a septum formed therein for administration, withdrawal or exchange of fluids with the target site, the housing having a side wall extending from the entry site to a base;
- a needle-penetrable region adjacent to and spanning substantially a majority of a perimeter of said implantable port, wherein the needle-penetrable region comprises a needle-penetrable material configured to allow complete penetration by a needle to attach a suture, said needle-penetrable material extending from the base and from a portion of the side wall for a selected distance.

7. The implantable port of claim 6, wherein the needle-penetrable material extends below the base.

8. The implantable port of claim 6, wherein the needle-penetrable material extends above the base.

9. The implantable port of claim 6, wherein the needle-penetrable region is devoid of any preformed spaces not containing the needle-penetrable material between the housing and the base.

10. The implantable port of claim 6, wherein the needle-penetrable material comprises a flexible polymer.

11. The implantable port of claim 10, wherein the flexible polymer comprises silicone.

12. The implantable port of claim 6, wherein the needle-penetrable region does not extend continuously along a cross-section of a bottom surface of the implantable port, the cross-section defined by a perimeter of the bottom surface.

13. The implantable port of claim 6, wherein the side wall is comprised of a metal material.

14. The implantable port of claim 6, wherein the needle-penetrable material does not contact the septum.

15. The implantable port of claim 6, wherein said implantable port includes a bottom surface, wherein the bottom surface is formed by the needle-penetrable material.

* * * * *